United States Patent [19]

Speier

[11] 4,125,552
[45] Nov. 14, 1978

[54] PREPARATION OF ALKYL POLYSULFIDES
[75] Inventor: John L. Speier, Midland, Mich.
[73] Assignee: Dow Corning Corporation, Midland, Mich.
[21] Appl. No.: 644,482
[22] Filed: Dec. 29, 1975
[51] Int. Cl.$^2$ ............................. C07F 7/08; C07F 7/18
[52] U.S. Cl. ................................. 260/448.8 R; 560/18; 560/125; 260/448.2 E; 260/448.2 N; 560/147; 570/264; 560/231; 562/594; 562/432; 562/507; 260/593 R; 260/608; 260/590 R
[58] Field of Search ................. 260/448.8 R, 448.2 E, 260/514 R, 515 M, 470, 481 R, 590, 593 R, 611 A, 614 R, 618 R, 632 R, 609 R

[56] References Cited
U.S. PATENT DOCUMENTS

| 3,842,111 | 10/1974 | Meyer-Simon et al. | 260/448.2 E |
| 3,849,471 | 11/1974 | Omietanski et al. | 260/448.2 E |
| 3,946,059 | 3/1976 | Janssen et al. | 260/448.2 E |

Primary Examiner—Paul F. Shaver
Attorney, Agent, or Firm—Robert F. Fleming

[57] ABSTRACT

Alkyl polysulfides are prepared by reacting alkyl halides with hydrogen sulfide and sulfur in the presence of ammonia or certain monoamines.

5 Claims, No Drawings

PREPARATION OF ALKYL POLYSULFIDES

BACKGROUND OF THE INVENTION

Applicant's copending application Ser. No. 557,214, filed Mar. 10, 1975 relates to the preparation of mercaptans by reacting alkyl halides with H₂S in the presence of ammonia or certain amines. The present application covers the addition of sulfur to this reaction to produce polysulfides.

It is known that alkyl polysulfides can be prepared by three general methods. One is the reaction of alkyl halides with metal polysulfides such as sodium polysulfide, the second is the reaction of mercaptans with sulfur and the third is the oxidation of mercaptans. Publications showing these various methods are as follows: for oxidation of mercaptans, G. A. Gornowicz and J. L. Speier, "Mechanisms of the Reactions of Sulfur Compounds", Vol. 3, page 55, 1968; for reaction of alkyl halides with metal polysulfides U.S. Pat. No. 3,842,111 and for the reaction of mercaptans with sulfur German OLS No. 2,405,758.

In addition, U.S. Pat. No. 3,849,471 relates to the reaction of alkyl halides with hydrogen sulfide in the presence of ethylene diamine to give alkyl mercaptans. This patent teaches, Table 3, column 9, that the reaction does not go appreciably in the presence of other amines such as tributyl amine, pyridine, and diethylene triamine (DETA). In Example 26 of the patent, the reaction of gamma-chloropropyltrimethoxysilane with hydrogen sulfide and sulfur in the presence of ethylene diamine is shown to give the corresponding disulfide. However, based upon the teachings of this patent that the reaction to form mercaptans does not go to any practical extent in the presence of other amines, it is not obvious that the process of this invention could be carried out.

DESCRIPTION OF THE INVENTION

This invention relates to a method of producing polysulfides containing the linkage —CS$_x$C— which comprises reacting (A) a halide of the formula RX$_a$ with (B)(1) a mixture of ammonia or a hydrocarbyl amine containing one N atom, no more than 6 atoms and being free of aliphatic unsaturation and having a K$_a$ of less than 1 × 10⁻⁹ in aqueous solution, (2) H₂S and (3) sulfur in amount of at least two moles of (A) per mole of (2) and at least one mole of sulfur per mole of (2), at a temperature of from 0° to 175° C. under autogenous pressure whereby a compound of the formula RS$_x$R or (—RS$_x$—)$_c$ is formed, in which process R is selected from the group consisting of aliphatic, cycloaliphatic or aralkyl hydrocarbon radicals free of aliphatic unsaturation, such hydrocarbon radicals substituted with alkoxy, keto, carboxyl, hydroxyl, —COOR³ or —OOCR³ in which R³ is a monovalent hydrocarbon radical free of aliphatic unsaturation, and silylated hydrocarbon radicals of the formula

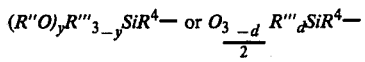

in which
R″ is an alkyl or an alkoxyalkyl radical of 1 to 6 carbon atoms,
R‴ is a monovalent hydrocarbon radical free of aliphatic unsaturation, a haloaryl radical or R$_f$CH₂CH₂— in which R$_f$ is a perfluoroalkyl radical,
R⁴ is a divalent or trivalent aliphatic, cycloaliphatic or aralkyl radical free of aliphatic unsaturation,
y is 1 to 3, and
d is 0 to 2,
X is bromine or chlorine, and
a is 1 or 2,
x is 2 to 6, and
c is an integer of at least 2.

It can be seen that the halide reactant (A) can contain 1 or 2 halogen atoms and that these can be chlorine or bromine or a combination thereof. The halogen atom is attached to an aliphatic or cycloaliphatic carbon atom and R is free of aliphatic unsaturation. R then, can be any alkyl radical such as methyl, ethyl, propyl, isopropyl, hexyl or octadecyl, or any cycloaliphatic hydrocarbon radical such as cyclopentyl, cyclobutyl, cyclohexyl or methylcyclohexyl, or any aralkyl hydrocarbon radical such as benzyl, β-phenylethyl, 2-phenylpropyl, β-xenylethyl, gamma-naphthylpropyl and the like. Typical halides, then, are ethylenechloride, 1,3-propylene dibromide and 1-chloro-3-bromocyclohexane.

In addition, the reactant (A) can be substituted with one or more of the defined substituents so that (A) can be a haloether such as chloromethylmethyl ether, chloroethyl-ethyl ethers, bis-chloromethyl ether, chlorobutylmethyl ether, chloromethylphenyl ether or chloromethylbenzyl ether; or halogenated ketones such as bromomethylmethyl ketone, chloromethylethyl ketone, chloromethylphenyl ketone, chloroethylbenzyl ketone or bis-chloroethyl ketone; halogenated carboxylic acids such as chloro acetic acid, α-chloropropionic acid, β-bromopropionic acid, gamma-chlorobutyric acid, or chlorocyclohexyl carboxylic acid. It should be understood, of course, that the products formed by the reaction of a halogenated acid produces the corresponding ammonium or amine salt. The free acid can be obtained by reacting this salt with a strong acid such as hydrochloric, etc. In addition, (A) can be a halo alcohol such as β-chloroethanol, β-chloropropanol, or bromohexanol. (A) can be an ester of a halogenated carboxylic acid which ester contains the group —COOR³ in which R³ is a monovalent hydrocarbon radical such as methyl, ethyl, isopropyl, butyl, phenyl, cyclohexyl or benzyl or (A) can be a carboxylic acid ester of a halo alcohol which ester contains the group —OOCR³ in which R³ is as above described.

In addition, (A) can be a silane of the formula

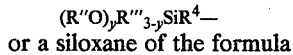

or a siloxane of the formula

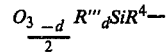

in which silanes and siloxanes R″ is any alkyl radical such as methyl, ethyl, isopropyl, butyl or hexyl or any alkoxyalkyl radicals such as —OCH₂CH₂OCH₃ or O(CH₂CH₂O)₂C₂H₅ and R‴ is any monovalent hydrocarbon radical free of aliphatic unsaturation such as methyl, ethyl, isopropyl, butyl, phenyl, xenyl, naphthyl, benzyl, β-phenylethyl, 2-phenylpropyl, or cyclohexyl; any haloaryl radical such as chlorophenyl, dichlorophenyl, chloroxenyl, or chloroanthracyl, or fluorinated hydrocarbon radicals of the formula R$_f$CH₂CH₂— in which R$_f$ is any perfluoroalkyl radical such as perfluoromethyl, perfluoroethyl, perfluorobutyl, perfluoroisobutyl or perfluorooctyl. The divalent radical $R^4$ between the halogen and the silicon can be any divalent aliphatic hydrocarbon radical such as methylene, dimethylene, trimethylene, isobutylene or octadecamethylene or any cycloalkylene radical such as cyclohexylene, methylcyclohexylene, cyclopentylene or cyclobutylene or any aralkylene radical in which the silicon is attached to the aromatic ring, such as benzylene, —C$_6$H$_4$CH$_2$CH$_2$—,

or —CH$_2$CH$_2$C$_6$H$_4$CH$_2$—. $R^4$ can also be trivalent radicals of the above type in which case $a$ has a value of 2. When $a$ is 2, the products are polymeric materials of the unit formula $(-R^4S_x-)_c$ in which $x$ is 2 or more and $c$ is an integer of at least 2.

The siloxanes employed as reactants can be homopolymers or copolymers and they can have either 1, 2 or 3 organic radicals substituted on the silicon atoms. Also these siloxanes can contain some silicon-bonded hydroxyl groups and some copolymerized organosiloxane units, which are free of reactive halogenated units, of the formula

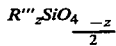

in which R"" is as above defined and $z$ is 0 to 3, such as, for example, dimethylsiloxane units, phenylmethylsiloxane units, trimethylsiloxane units trifluoropropylmethylsiloxane units, diphenylsiloxane units, monophenylsiloxane units, monomethylsiloxane units, or SiO$_2$ units. Of course, in these copolymers there should be at least one siloxane unit having the defined —R"X$_a$ substituents and the total number of X groups per molecule should be no more than two. Such copolymers are considered to be within the claimed process.

Reactant (1) employed in this invention can be ammonia or any hydrocarbon amine containing one N atom and no more than 6 carbon atoms which is free of aliphatic unsaturation and has a $K_a$ of less than $1 \times 10^{-9}$. This means that the amines are those in which the nitrogen is attached to aliphatic or cycloaliphatic carbon atoms. Specific examples of such amines are primary amines such as methyl amine, butyl amine, isopropyl amine, cyclohexyl amine and cyclopentyl amine; secondary amines such as dimethyl amine, dipropyl amine and methylbutyl amine and tertiary amines such as trimethyl amine, triethyl amine or ethyldimethyl amine. The total number of carbon atoms in the amine should be no more than 6.

Were $a$ is one, the overall reaction goes according to the equation

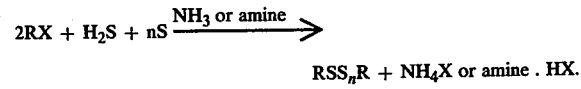

Thus, there should be at least two moles of halide per mole of H$_2$S and at least one mole of S per mole of H$_2$S. The number of S atoms ($x$) in the polysulfide linkage depends upon the molar ratio of S to H$_2$S. Equivalent amounts give the disulfide ($x = 2$) whereas three moles of S per mole of H$_2$S produces the tetrasulfide ($x = 4$) etc. When the halide has two halogen atoms, the overall equation becomes

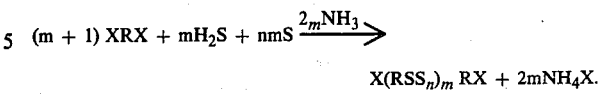

The reaction of this invention is best carried out at a temperature from 0° to 175° C. under autogenous pressure. The optimum temperature to be employed with any particular type of reagent varies. The pressure, of course, will vary with the temperature and the volatility of the reactants. If desired, external pressure can be applied to the system, but this is unnecessary because the autogenous pressure is sufficient for excellent yields.

In many cases, it is advantageous to employ a polar solvent in the reaction. Examples of operative polar solvents are water, alcohols such as methanol, ethanol, isopropanol, or butanol, ethers, such as dioxane, the dimethyl ether of ethylene glycol or the monomethyl ether of ethylene glycol, nitriles such as acetonitrile, or propionitrile; N,N-disubstituted amides such as dimethyl acetamide, or diethyl formamide. Obviously, the polar solvent should be non-acidic.

The utility of polysulfides generally is well known and in addition the silicon-containing polysulfides of this invention are useful as coupling agents between clay and rubber.

The following examples are illustrative only and should not be construed as limiting the invention which is properly delineated in the appended claims. In the examples the following abbreviations are used: Me for methyl, Et for ethyl, Pr for propyl and Ph for phenyl.

EXAMPLE 1

1.5 mole sulfur, 6 moles of ammonia and 1.5 mole of hydrogen sulfide were charged into a 3 liter stainless steel autoclave and heated to 70° C. as 3 moles of n-hexyl chloride and 250 ml. of methanol were pumped into the vessel. After 2 hours at 70° C., the mixture was filtered free of ammonium chloride and the filtrate was distilled to give an 83.5 percent yield of di-n-hexyl disulfide, boiling point 120° – 122° C. and 1 mm. n$_D^{25}$ 1.4864, d$_4^{25}$ 0.9145, R$_D$ 0.341, calculated R$_D$ 0.315.

A higher boiling residue was essentially di-n-hexyl trisulfide which was obtained in 10 percent yield.

EXAMPLE 2

This example shows the preparation of a polymeric sulfide. 3.3 moles of sulfur, 12 moles of ammonia and 3.4 moles of hydrogen sulfide were charged into a 3 liter stainless steel autoclave which was then heated to 60° C. 1,2-dichloroethane (3 moles) and 250 ml. of methanol were pumped into the vessel. The temperature rose to 134° C. during this addition. After 3 hours the temperature fell to 80° C. and the autoclave was opened. The product was a gray-green solid which was extracted three times with hot water to remove ammonium chloride, rinsed with methanol and dried to give a 98.5 percent yield of the polymer (C$_2$H$_4$S$_2$)$_c$.

EXAMPLE 3

Two moles of sulfur were charged into a 3 liter stainless steel autoclave which was then evacuated. 7.9 moles of ammonia and 2.1 moles of hydrogen sulfide were added. The mixture was heated to 70° C. and 100 ml. of methanol and 4 moles of 3-chloropropyltrimethoxysilane were pumped into the vessel followed by 87 ml. of methanol to flush out the pump and lines. The vessel was maintained near 70° C. The reaction was found to be essentially complete after 2.1 hours. After 2.6 hours the mixture was filtered free of ammonium chloride, washed with hexane and dried. The filtrate and the hexane washes were combined and stripped of volatiles on a rotary evaporator at 50° C. at 20 mm. The product was filtered again to obtain a clear, light liquid having a refractive index of 1.4662 and a viscosity of 16 centipoises at 25° C. This material was essentially pure { $(CH_3O)_3Si(CH_2)_3$ } $_2S_2$.

EXAMPLE 4

7.5 moles of sulfur, 250 ml. of methanol and 5 moles of 3-chloropropyl trimethoxysilane was charged into a three liter stainless steel autoclave. 7 moles of ammonia and 2.56 moles of hydrogen sulfide were added and the autoclave was heated at 70° C. for 2½ hours. The product was worked up as in Example 3 to obtain 1,074.4 g. of a cloudy, yellow liquid which was a mixture of the formula
{ $(CH_3O)_3Si(CH_2)_3$ } $_2S_x$
having the properties $n_D^{25}$ 1.5130, $d_4^{25}$ 1.1865, $R_D$ 0.2533, calculated $R_D$ 0.2509. NMR analysis showed the product to be a mixture of sulfides in which $x$ is 2, 3, 4 and 5 in the molar ratio of 1:2.3:1.1:1.1 respectively.

EXAMPLE 5

0.23 mole of sulfur was placed in an autoclave which was evacuated and 1.5 mole of dimethyl amine and 0.25 mole of hydrogen sulfide were added. The vessel was heated to 100° C. and 0.4 mole of 3-chloropropyl-dimethyl-methoxysilane was added and after 18 hours at 100° C. the reaction was complete. The product was a clear, yellow fluid which was 98 percent { $CH_3O(CH_3)_2Si(CH_2)_3$} $_2S_2$ with the properties of $n_D^{25}$ 1.4812, $d_4^{25}$ 0.9797, $R_D$ 0.2906, calculated $R_D$ 0.2896.

EXAMPLE 6

Equivalent results are obtained when cyclohexyl amine is substituted for the triethyl amine of Example 1.

EXAMPLE 7

Di or polysulfides are obtained when the following halides are reacted with a mixture of ammonia, $H_2S$ and S in the mole ratio of two moles halide, one mole $H_2S$ and one mole S at 100° C. under autogenous pressure.

| Halide | Disulfide |
|---|---|
| MeCOOCH$_2$CH$_2$Cl | {MeCOOCH$_2$CH$_2$S—}$_2$ |
| MeCOCH$_2$Cl | {MeCOCH$_2$S—}$_2$ |
| EtOC$_2$H$_4$Cl | {EtOC$_2$H$_4$S—}$_2$ |
| Br(CH$_2$)$_3$COOH | {—S(CH$_2$)$_3$COONH$_4$}*$_2$ |
| ClCH$_2$CH$_2$OH | {—SCH$_2$CH$_2$OH}$_2$ |
| ClCH$_2$COOEt | {—SCH$_2$COOEt}$_2$ |
| ClCH$_2$CH$_2$Si(OEt)$_3$ | {—SCH$_2$CH$_2$Si(OEt)$_3$}$_2$ |
| ClCH$_2$Si(OPr)$_3$ | {—SCH$_2$Si(OPr)$_3$}$_2$ |
| 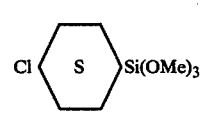 | |
| ClCH$_2$CHClCH$_2$CH$_2$Si(OMe)$_3$ | {—CH$_2$CHS$_2$}$_n$ with pendant CH$_2$–CH$_2$–Si(OMe)$_3$ |
| C$_{12}$H$_{25}$Cl | {C$_{12}$H$_{25}$S—}$_2$ |
| PhCH$_2$Cl | {PhCH$_2$S—}$_2$ |
| (MeO)$_2$MeSi(CH$_2$)$_3$Cl | {(MeO)$_2$MeSi(CH$_2$)$_3$S—}$_2$ |
| Cl(CH$_2$)$_3$Si(Ph)(OMe)$_2$ | {—S(CH$_2$)$_3$Si(Ph)(OMe)$_2$}$_2$ |
| 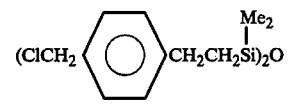 | |
| Cl(CH$_2$)$_3$(CF$_3$CH$_2$CH$_2$)Si(OCH$_2$CH$_2$OMe)$_2$ | {—S(CH$_2$)$_3$(CF$_3$CH$_2$CH$_2$)Si(OCH$_2$CH$_2$OMe)$_2$}$_2$ |
| {Cl(CH$_2$)$_3$SiMe$_2$O}$_2$Si(OSiMe$_3$)$_2$ | {—S$_2$(CH$_2$)$_3$SiMe$_2$OSiOSi(CH$_2$)$_3$—}$_2$ with {O–Si–Me$_3$}$_2$ |
| BrCH$_2$SiMe$_2$—O—SiMe(OSiMe$_3$)$_2$ | {—SCH$_2$SiMe$_2$—O—SiMe(OSiMe$_3$)$_2$}$_2$ |

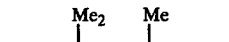

-continued

| Halide | Disulfide |
|---|---|
| $\begin{array}{cc} Me_2 & Me_2 \\ \mid & \mid \\ ClCH_2Si-O-SiOSiMe_3 \end{array}$ | $\{\begin{array}{cc} Me_2 & Me_2 \\ \mid & \mid \\ -SCH_2Si-O-SiOSiMe_3 \end{array}\}_2$ |

*Acid recovered by reacting with HCl.

EXAMPLE 8

Equivalent results are obtained when the following amines are used in the place of ammonia in the procedure of Example 1: $Me_3N$, $Et_3N$ and $Pr_2NH$.

That which is claimed is:

1. A method of producing sulfides containing the linkage $CS_xC$ which comprises reacting (A) a halide of the formula $RX_a$ with (B) a mixture of (1) ammonia or a hydrocarbyl amine containing one nitrogen atom, no more than 6 carbon atoms and having a $K_a$ of less than $1 \times 10^{-9}$ in aqueous solution, (2) $H_2S$ and (3) sulfur in amount of at least two moles of (A) per mole of (2) and at least one mole of sulfur per mole of (2), at a temperature of from 0° to 175° C. under autogenous pressure whereby a compound of the formula $RS_xR$ or $(-RS_x-)_c$ is formed in which process R is of the group consisting of aliphatic, cycloaliphatic or aralkyl hydrocarbon radicals free of aliphatic unsaturation, such hydrocarbon radicals substituted with alkoxy, keto, carboxy, hydroxy, $-COOR^3$ or $-OOCR^3$ radicals in which $R^3$ is a monovalent hydrocarbon radical free of aliphatic unsaturation and silylated hydrocarbon radicals of the formula $(R''O)_y R'''_{3-y} SiR^4-$ and $O_{\frac{3-d}{2}} R'''_d SiR^4-$ in which
   $R''$ is an alkyl or alkoxyalkyl radical of 1 to 6 carbon atoms,
   $R'''$ is a monovalent hydrocarbon radical free of aliphatic unsaturation, a haloaryl radical or $R_f CH_2 CH_2-$ in which $R_f$ is a perfluoroalkyl radical,
   $R^4$ is a divalent or trivalent aliphatic, cycloaliphatic or aralkyl hydrocarbon radical free of aliphatic unsaturation,
   $y$ is 1 to 3,
   $d$ is 0 to 2,
   X is bromine or chlorine,
   $x$ is 2 to 6,
   $a$ is 1 to 2, and
   $c$ is an integer of at least 2.

2. The process of claim 1 which is carried out in the presence of a polar solvent.

3. The process of claim 2 in which the polar solvent is methanol.

4. The process of claim 3 in which (A) is 3-chloropropyltrimethoxysilane and (B)(1) is ammonia.

5. The process of claim 1 in which R is a silylated hydrocarbon radical.

* * * * *

UNITED STATES PATENT AND TRADEMARK OFFICE
CERTIFICATE OF CORRECTION

PATENT NO. : 4,125,552
DATED : November 14, 1978
INVENTOR(S) : John L. Speier

It is certified that error appears in the above-identified patent and that said Letters Patent are hereby corrected as shown below.

In Column 1, line 44; the line reading "containing one N atom, no more than 6 atoms and being" should read "containing one N atom, no more than 6 carbon atoms and being".

In Column 6, line 9; the word reading "dimethyl-methoxysilane" should read "dimethylmethoxysilane".

In Column 6, line 12; the line reading "$CH_3O(CH_3)_2Si(CH_2)_3\}_2S_2$ with the properties of $n_D^{25}$" should read "$CH_3O(CH_3)_2Si(CH_2)_3\}_2S_2$ with the properties $n_D^{25}$".

Signed and Sealed this

Twenty-fourth Day of November 198.

[SEAL]

Attest:

GERALD J. MOSSINGHOFF

Attesting Officer    Commissioner of Patents and Trademarks